United States Patent
Ma et al.

(10) Patent No.: US 10,105,173 B2
(45) Date of Patent: Oct. 23, 2018

(54) RADIO FREQUENCY GENERATOR AND A METHOD OF GENERATING RADIO FREQUENCY ENERGY UTILIZING THE RADIO FREQUENCY GENERATOR

(71) Applicant: Mianyang Lide Electronics Co., Ltd, Sichuan (CN)

(72) Inventors: Fu Ma, Sichuan (CN); Xiang Jing, Tianjin (CN); Gang Dong, Henan (CN); Xilin Du, Shaanxi (CN); Xuequan Huang, Chongqing (CN); Zhechuan Mei, Chongqing (CN); Wei Zhang, Sichuan (CN)

(73) Assignee: Mianyang Lide Electronics Co., Ltd, Sichuan (CN)

( * ) Notice: Subject to any disclaimer, the term of this patent is extended or adjusted under 35 U.S.C. 154(b) by 24 days.

(21) Appl. No.: 15/375,419

(22) Filed: Dec. 12, 2016

(65) Prior Publication Data
US 2017/0164995 A1    Jun. 15, 2017

(30) Foreign Application Priority Data
Dec. 15, 2015 (CN) .......................... 2015 1 0930219

(51) Int. Cl.
*H03F 1/00* (2006.01)
*A61B 18/12* (2006.01)
(Continued)

(52) U.S. Cl.
CPC ..... *A61B 18/1206* (2013.01); *H02M 7/53871* (2013.01); *H03F 1/0227* (2013.01); *H03F 3/193* (2013.01); *H03F 3/213* (2013.01); *A61B 2018/00577* (2013.01); *A61B 2018/00601* (2013.01); *A61B 2018/00607* (2013.01); *A61B 2018/00642* (2013.01); *A61B 2018/00648* (2013.01); *A61B 2018/00702* (2013.01); *A61B 2018/00767* (2013.01); *A61B 2018/00779* (2013.01); *A61B 2018/00827* (2013.01);
(Continued)

(58) Field of Classification Search
CPC ..... H03F 1/00; H03F 1/36; H03F 1/40; H03F 3/00; H03F 1/3217; H03F 3/2173; H03F 3/26; H03F 1/0227; H03F 3/193; H03F 3/02; G05B 7/02; G05B 9/03; G05B 9/05; A61B 18/1206; H02M 7/53871
USPC .................................................. 330/1 R, 1 A
See application file for complete search history.

(56) References Cited

U.S. PATENT DOCUMENTS

2015/0207433 A1* 7/2015 Liu .................. H02M 1/40
                                                   363/132
2016/0248343 A1* 8/2016 Garrity ............. H02J 3/383

* cited by examiner

*Primary Examiner* — Khanh V Nguyen
(74) *Attorney, Agent, or Firm* — Maier & Maier, PLLC

(57) ABSTRACT

A radio frequency generator, includes an input voltage unit, a smart power unit, a voltage acquisition unit, a power amplifier unit, an output unit, a load unit, a current acquisition unit, a processor unit, a signal transmission and drive unit and an input control unit. The present application combined advantages of the high-frequency electric knife and the radio frequency ablation device, can be used for both cutting and coagulating the target tissue, and the ablation or treatment to the target tissue. This radio frequency generator has high versatility, can be used as standard component to produce and manufacture. Different medical radio frequency manufacturers can produce and manufacture their own products to meet clinical needs of different clients and different departments for example, by changing a small quantity of peripheral circuits or software.

11 Claims, 7 Drawing Sheets

(51) Int. Cl.
  *H03F 1/02*     (2006.01)
  *H03F 3/193*    (2006.01)
  *H03F 3/213*    (2006.01)
  *H02M 7/5387*   (2007.01)
  *A61B 18/00*    (2006.01)
  *H02M 1/00*     (2006.01)
(52) U.S. Cl.
  CPC ............... *A61B 2018/00875* (2013.01); *A61B 2018/00892* (2013.01); *A61B 2018/1266* (2013.01); *H02M 2001/007* (2013.01); *H03F 2200/351* (2013.01); *H03F 2200/451* (2013.01); *H03F 2200/541* (2013.01)

RADIO FREQUENCY GENERATOR AND A METHOD OF GENERATING RADIO FREQUENCY ENERGY UTILIZING THE RADIO FREQUENCY GENERATOR

TECHNICAL FIELD

The invention relates to a radio frequency (RF) generator and a method of generating RF energy utilizing the radio frequency generator.

DISCUSSION OF RELATED ART

Medical radio frequency generator is the core components of hardware of high frequency surgical equipment, which is also known as the medical high-frequency generator. High-frequency surgical equipment are widely used in ablation, coagulation and cutting to the target tissue. Currently, high-frequency surgical equipment have become indispensable medical electronic devices of surgery or minimal invasive tumor treatment.

Currently, for various kinds and brands of high-frequency surgical equipment on the market, the high-frequency generator can be divided into two categories: one category is the device represented by high-frequency electric knife. Another is the device represented by radio frequency ablation system.

The device represented by high-frequency electric knife has no power amplifier unit, and uses the structure that high-frequency power oscillator converts input power into required frequency and power directly. Wherein, high-frequency power oscillator mainly has three forms: spark oscillator, tube-type oscillator, and solid oscillator. The basic structure of high frequency electric knife is shown as FIG. 1. Since there is no high frequency power amplifier unit, it adjusts the output power by interval time for oscillating. The features of high-frequency electric knife are: (1) High output voltage, and the maximum open circuit peak-peak voltage value Vp-p can be up to thousands of volts. (2) Large range of adaptive load impedance, the load from 30Ω-1500Ω can achieve the desired output power. The curve that the set power of high-frequency electric knife varies with load is shown as FIG. 5-1. (3) Wide application for departments, almost all of the departments can use it for cutting and coagulating the corresponding target tissue. (4) But not fit for the ablation and treatment to the target tissue, including cardiac ablation, liver tumor ablation, thyroid ablation and treatment. The reason for this is that: (1) The output voltage has been in a high state and the voltage value is relatively constant, the output power is only relevant to its interval time. The output waveforms of high-frequency electric knife under different power settings when the load is 100Ω are shown in FIG. 7-1, FIG. 7-2 and FIG. 7-3. Whether cardiac ablation or hepatic tumor ablation, the impedance of lesions tissue mainly focus on the low resistance areas, when the high voltage mentioned above injects into the lesions, the tissue around the electrodes will carbonize within a very short period of time, and the energy cannot continue to inject into the lesions, cannot achieve the expected ablation range, and accompanied by dramatic sparks, there are enormous potential risks. (2) In order to adjust the output power, in addition to the main frequency (200 KHz-1000 KHz), also includes low-frequency modulation wave with a frequency of $f=1/(T_{ON}+T_{OFF})$, the frequency is mostly selected in the range of 10 KHz-30 KHz, the current of this frequency range has a certain stimulation effect on humans' muscles and nerves.

The device represented by radio frequency ablation system uses the structure that power amplifier unit converts input power into required frequency and power. High frequency power amplifier unit mainly has four forms: Class A, Class B, Class AB, and Class C. The basic structure of radio frequency ablation instrument is shown as FIG. 2. The features of existing radio frequency ablation device are: (1) To reduce the stimulation to the muscles and nerves, and to reduce or avoid the carbonation of the tissue near the treatment electrode, continuous high frequency equiamplitude wave must be output in constant power mode. Therefore, the power adjustment method of high-frequency electric knife is not fit for the radio frequency device for ablation or treatment. (2) Power amplifier unit is simulation amplifier, that is, the power amplifier tube is like a variable resistance, the greater the amplitude of the high-frequency drive signal, the more the power amplifier tube opens, the smaller the on-resistance, the greater the output current flowing through, and the greater the power obtained by the load; the smaller the amplitude of the high-frequency drive signal, the smaller the power amplifier tube opens, the larger the on-resistance, the smaller the output current flowing, and the smaller the power obtained by the load; Due to the larger loss of power amplifier tube, heat radiating measures by using larger radiator, cooling fan, etc. are required. (3) Low output voltage, maximum open circuit peak-peak voltage value $V_{p-p}$ is usually below 800V. Due to the radio frequency ablation system mainly work in low resistance area, the output voltage cannot be too high. If the voltage is too high, the purpose of ablation or treatment for lesions cannot be achieved. (4) The load impedance range of constant power area is small and concentrated in low resistance area. Take liver radio frequency ablation devices as an example, its constant-power load range is 10Ω-150Ω. To increase the upper limit value of constant-power load range, the direct current (DC) input voltage of power amplifier unit must be increased, so that when works in low impedance area, the power amplifier tube of simulation power amplifier unit need to withstand higher tube voltage drop, the power consumption is increased, and the reliability is further reduced. (5) Load impedance ranges of constant power areas of radio frequency products for different departments vary enormously. The curve that the set power of liver radio frequency ablation varies with load is shown as FIG. 5-2. (6) Especially suit for ablation or treatment to corresponding target tissue. (7) Due to the maximum output voltage is lower, after impedance rises, the output power decline sharply, the power gained by the load in the high impedance area is very little, and the target tissue cannot be cut.

To sum up, the load of high-frequency electric knife from 30Ω-1500Ω can achieve the desired output power. Apply widely for departments, almost all of the departments can use it for cutting and coagulating the corresponding target tissue, but not suit for the ablation and treatment to the target tissue. However, the constant power load range of the radio frequency ablation device is narrow, mainly works in specific impedance area such as low impedance, etc., particularly well suits for the ablation or treatment to its corresponding target tissue, but the target tissues cannot be cut.

SUMMARY

The purpose of the present invention is to provide a radio frequency generator, and a method of generating radio frequency energy using the radio frequency generator, it can be used for both cutting and coagulating the target tissue, and the ablation or treatment to the target tissue.

To solve the technical matters above, the present invention provides a radio frequency generator, including an input voltage unit, a smart power unit, a voltage acquisition unit, a power amplifier unit, an output unit and a load unit connected in sequence; a processor unit is connected between the voltage acquisition unit and the power unit; a current acquisition unit is set between the power amplifier unit and the processor unit; wherein, the input voltage unit is used for providing DC voltage to the smart power unit; the smart power unit is used for providing variable DC voltage to the power amplifier unit; the voltage acquisition unit is used to collect the actual output voltage of the smart power unit; the current acquisition unit is used to collect the actual output current of the smart power unit; the processor unit is used to obtain the actual output power of the smart power unit, and the actual impedance and obtained actual power of the load unit, based on the collected actual output voltage and actual output current, compare the actual output power of the smart power unit and the actual impedance of the load unit with the preset value respectively, and adjust the output voltage or output power of the smart power unit based on the result of comparison, to keep the actual output power of the smart power unit and the preset power consistent, to make the load unit get expected radio frequency energy; and a signal transmission and drive unit, is connected to a drive end of the power amplifier unit, to generate high-frequency drive signal to drive the power amplifier unit.

Furthermore, the output voltage value, the output current value and the output power value of the smart power unit are not fixed, but, can be adjusted freely according to the different needs of the outside.

Furthermore, the smart power unit is a switching power converter, including a first capacitor C21, a first transistor Q21, a second inductor L22, a third capacitor C23 connected in parallel in order; a first inductor L21 is connected in series between the positive end of the first capacitor C21 and the drain of the first transistor Q21, and the dotted terminal of the first inductor L21 is connected to the positive end of the first capacitor C21; the grid of the first transistor Q21 is connected to the PWM-end of the processor unit; a second capacitor C22 and a diode D21 are connected in series in order between the opposite terminal of the second inductor L22 and the third capacitor C23, and the cathode of the diode D21 is connected to the positive end of the third capacitor C23, the positive end of the second capacitor C22 is connected to the opposite terminal of the second inductor L22.

Furthermore, the voltage acquisition unit includes a first resistor R31 and a second resistor R32, which are connected with each other in series and connected to both ends of the third capacitor C23 in parallel, the connected node of the first resistance R31 and the second resistance R32 is connected to the voltage acquisition port of the processor unit.

Furthermore, the current acquisition unit includes a third resistor R41 connected to the power amplifier unit, the connected node of the third resistor R41 and the power amplifier unit is connected to the current acquisition port of the processor unit.

Furthermore, the output unit includes a high frequency isolation transformer, a monitoring and controlling unit of auxiliary electrode and therapeutic electrode.

Furthermore, the radio frequency generator further includes an input control unit connected to the processor unit for inputting control command.

A method of generating radio frequency energy using the radio frequency generator mentioned above, includes following steps:

S1: providing DC power for the power amplifier by the smart power unit, and collecting the actual output voltage and actual output current of the smart power unit, obtaining actual output power and real time equivalent impedance of the smart power unit based on the collected information, and calculating the actual impedance and obtained actual power of the load unit;

S2: comparing the actual output power of the smart power unit with the preset power, adjusting the duty cycle of the smart power unit based on the result of comparison, to make the output power of the smart power unit be constant to the preset power;

S3: comparing the actual impedance of the load unit with the threshold of preset impedance, automatically controlling the radio frequency energy to continue to output or to stop to output based on the comparison result.

Furthermore, step S1 includes the following steps:

S11: providing DC power for the power amplifier by the smart power unit, and collecting the actual output voltage and the actual output current of the smart power unit, to obtain the actual output voltage and the actual output current of the smart power unit;

S12: calculating the actual output power of the smart power unit based on $P_{20}=V*I$; calculating the actual impedance of the smart power unit based on $R_{20}=V/I$;

S13: according to the actual power obtained by the load unit $P_0=P_{20}-$(loss of the power amplifier+loss of the output unit), and the loss of the power amplifier and the loss of the output unit are known, and very small, the actual power obtained by the load unit can be calculated by the actual output power of the smart power unit.

S14: according to proportional relation between the primary and secondary windings of the high frequency isolation transformer in the output unit, the actual impedance of the load unit can be calculated by the actual impedance of the smart power unit.

Furthermore, the specific operations of step S2 is following:

S2: comparing the actual output power of the smart power unit with the preset power, when the actual output power of the smart power unit is greater than the preset power, reduce the duty cycle; when the actual output power of the smart power unit is less than the preset power, increase the duty cycle; keeping the actual output power of the smart power unit and the preset power consistent.

Furthermore, the specific operations of step S3 is following:

S3: comparing the actual impedance of the load unit with the threshold of the preset impedance, when the actual impedance of the load unit is greater than or equal to the lower threshold of the preset impedance and less than or equal to the upper threshold of the preset impedance, continue the radio frequency output; when the actual impedance of the load unit is less than the lower threshold of the preset impedance, the duty cycle of the smart power becomes zero, stop the radio frequency output; when the actual impedance of the load unit is greater than the upper threshold of the preset impedance, the duty cycle of the smart power becomes zero or minimum, stop the radio frequency output or reduce the radio frequency output.

The beneficial effects of the present invention are as follows: The present application combined advantages of high-frequency electric knife and radio frequency ablation device, can be used for both cutting and coagulating the target tissue, and the ablation or treatment to the target tissue. The hardware circuit of the present application has a wide load range of constant output power. When the present application is used for cutting and coagulating the target tissue, the maximum open circuit peak-peak voltage value $V_{p-p}$ is only a few hundred volts, sparks are few, carbonization level is less, potential risk is small, and low-frequency modulated wave which stimulates human tissue and nerve is not included. When the present application is used for the ablation or treatment to the target tissue, it can meet the clinical needs of different departments only by embedding the appropriate software. The novel radio frequency generator, during the energy conversion process has small own loss, low failure rate, and high reliability. The modes of data collection and energy control are simple, direct and reliable. Versatility is high, and can be used as standard components to produce and manufacture. Different medical radio frequency manufacturers can produce and manufacture their own products to meet clinical needs of different clients and different departments only by changing a small quantity of peripheral circuits or software.

BRIEF DESCRIPTION OF THE DRAWINGS

FIG. 5-1 is a curve graph that the output power of the high-frequency electric knife changes with load in different power settings.

FIG. 5-2 is a curve graph that the output power of the conventional radio frequency ablation device changes with load in different power settings.

FIG. 5-3 is a curve graph that the output power of the present invention changes with load in different power settings.

FIG. 6-1 is a curve graph that the DC input voltage value of high-frequency power oscillator unit of the high-frequency electric knife changes with load in different power settings.

FIG. 6-2 is a curve graph that the DC input voltage value of the power amplifier unit of the conventional radio frequency ablation device changes with load in different power settings.

FIG. 6-3 is a curve graph that the DC input voltage value of the power amplifier unit of the present invention changes with load in different power settings.

FIG. 7-1 is a waveform of output voltage waveform of the high-frequency electric knife when the power setting is 100% and the load is 100 Ω;

FIG. 7-2 is a waveform of output voltage waveform of the high-frequency electric knife when the power setting is 50% and the load is 100Ω;

FIG. 7-3 is a waveform of output voltage waveform of the high-frequency electric knife when the power setting is 10% and the load is 100Ω;

FIG. 8-1 is a waveform of output voltage waveform of the conventional radio frequency ablation device when the power setting is 100% and the load is 100Ω;

FIG. 8-2 is a waveform of output voltage waveform of the conventional radio frequency ablation device when the power setting is 50% and the load is 100Ω;

FIG. 8-3 is a waveform of output voltage waveform of the conventional radio frequency ablation device when the power setting is 10% and the load is 100Ω;

FIG. 9-1 is a waveform of output voltage waveform of the present invention when the power setting is 100% and the load is 100Ω;

FIG. 9-2 is a waveform of output voltage waveform of the present invention when the power setting is 50% and the load is 100Ω;

FIG. 9-3 is a waveform of output voltage waveform of the present invention when the power setting is 10% and the load is 100Ω;

FIG. 10-1 is a curve graph that the output power of the present invention combined with thyroid ablation software module changes with load in different power settings;

FIG. 10-2 is a curve graph that the output power of the present invention combined with cardiac ablation software module changes with load in different power settings;

FIG. 10-3 is a curve graph that the output power of the present invention combined with liver ablation software module changes with load in different power settings;

FIG. 10-4 is a curve graph that the output power of the present invention combined with gastrointestinal tract ablation software module changes with load in different power settings;

FIG. 10-5 is a curve graph that the output power of the present invention combined with cutting and coagulation software module changes with load in different power settings.

Wherein, 10. Input voltage unit; 20. Smart power unit; 30. Voltage acquisition unit; 40. Current acquisition unit; 50. Processor unit; 60. Signal transmission and drive unit; 70. Input control unit; 80. Power amplifier unit; 90. Output unit; 100. Load unit.

DETAILED DESCRIPTION OF THE EMBODIMENTS

Following is detailed description for the embodiments of the present invention, for the skilled in the art to understand this invention, but should be clear that the present invention is not limited by the scope of the detailed embodiments, and for the skilled in the art, so long as various changes are in the spirit and scope of the present invention which are limited and determined by the attached claims, these changes are obvious, all inventions and creations utilizing the concept of the present invention are in protection.

Figure 3:
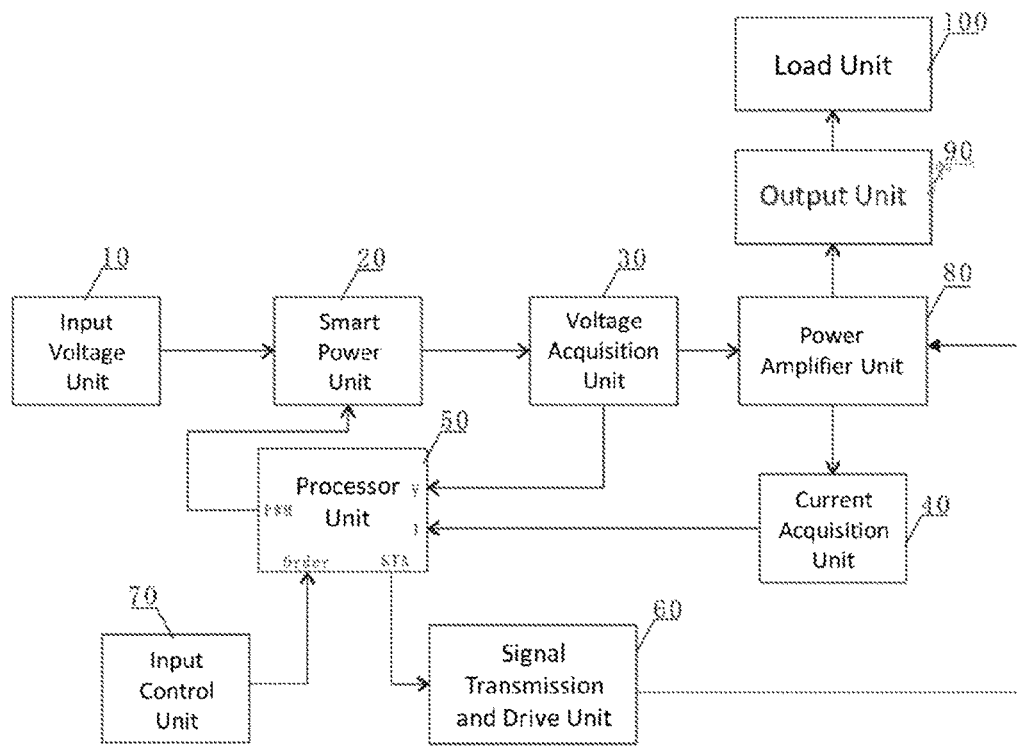
FIG. 3 is a schematic diagram of one embodiment of the present invention.
Figure 4:
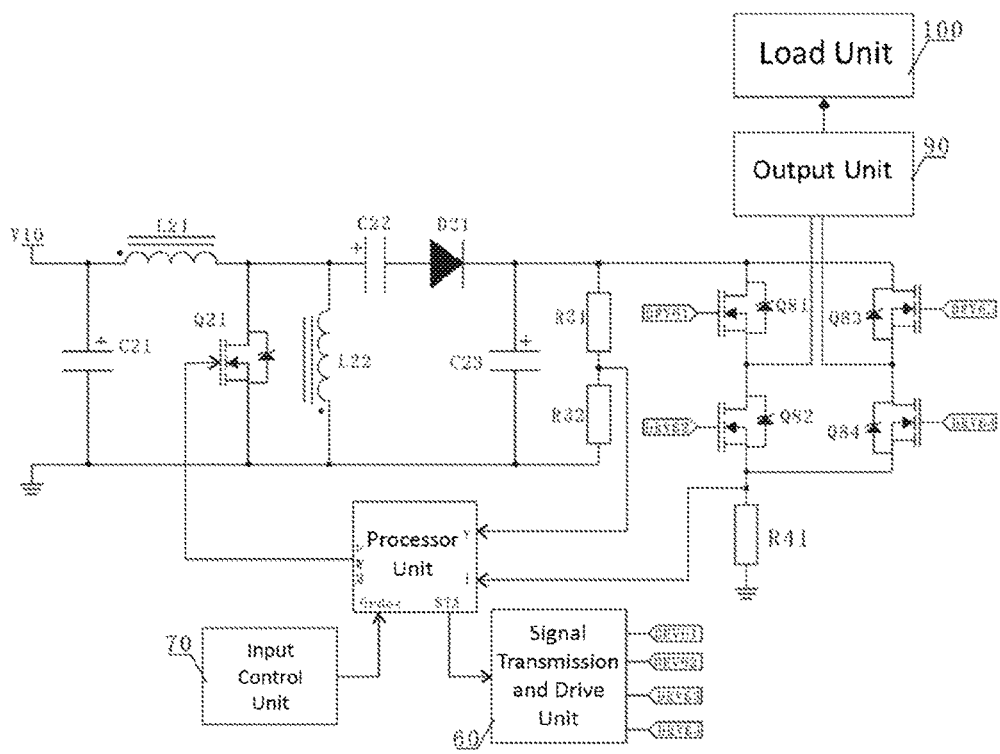
FIG. 4 is a schematic diagram of another embodiment of the present invention.
Figures 1, 5:
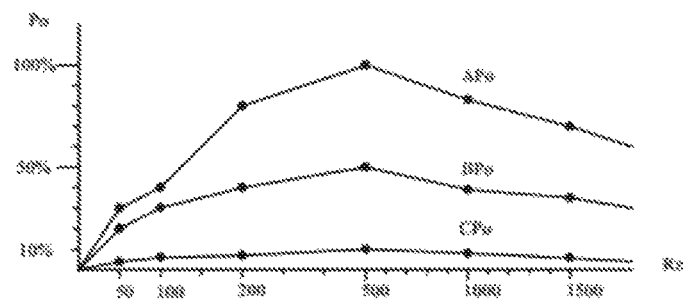
Figures 2, 5:
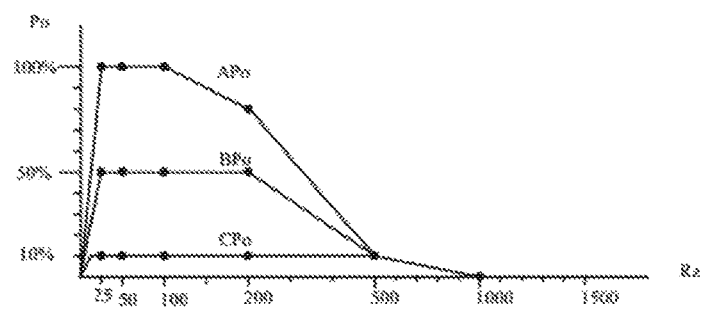
Figures 3, 5:
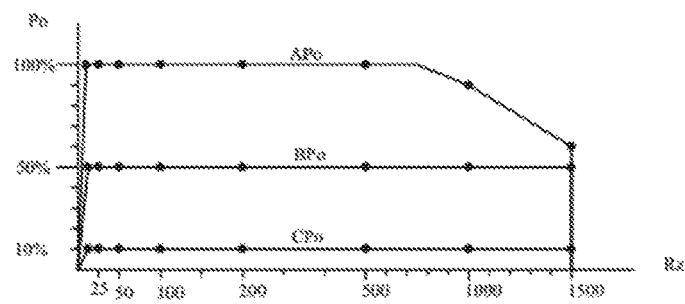

The radio frequency generator shown in FIG. 3 and FIG. 4, includes an input voltage unit 10, a smart power unit 20, a voltage acquisition unit 30, a power amplifier unit 80, an output unit 90, a load unit 100, a current acquisition unit 40, a processor unit 50, a signal transmission and drive unit 60 and an input control unit 70. Following is detailed description for each unit:

Wherein, the input voltage unit 10 includes a unit related to electromagnetic compatibility and a rectifier unit, is used for providing DC voltage to the smart power unit 20; the output unit 90 includes a high frequency isolation transformer, a monitoring and controlling unit of auxiliary electrode and therapeutic electrode; the power amplifier unit 80 is H-type full bridge drive circuit.

The smart power unit 20 is connected to the output end of the input voltage unit 10, uses a switching power converter topology, and is used for providing variable DC voltage to the power amplifier unit 80. The smart power is a switching power converter adjusted by a pulse width PWM. The output mode can be constant current, constant voltage, constant power, regardless of the output mode, DC power is provided for next level circuit, which is the power amplifier unit 80, in the detailed embodiments of present invention, the constant power output mode is adopted.

The detailed structure of the smart power unit 20 includes a first capacitor C21, a first transistor Q21, a second inductor L22, a third capacitor C23 connected in parallel in order; Between the positive end of the first capacitor C21 and the drain of the first transistor Q21, a first inductor L21 is connected in series, and the dotted terminal of the first inductor L21 is connected to the positive end of the first capacitor C21; The grid of the first transistor Q21 is connected to the PWM-end of the processor unit 50; Between the opposite terminal of the second inductor L22 and the third capacitor C23, a second capacitor C22 and a diode D21 are connected in series in order, and the cathode of the diode D21 is connected to the positive end of the third capacitor C23, the positive end of the second capacitor C22 is connected to the opposite terminal of the second inductor L22.

The voltage acquisition unit 30 includes a first resistor R31 and a second resistor R32, which are connected with each other in series and connected to both ends of the third capacitor C23 in parallel, the connected node of the first resistance R31 and the second resistance R32 is connected to the voltage acquisition port of the processor unit 50. the voltage acquisition unit 30 is used for feeding the actual output voltage value of the smart power unit 20 back to V port of the processor unit 50.

The current acquisition unit 40 includes a third resistor R41 connected to the power amplifier unit 80, the connected node of the third resistor R41 and the power amplifier unit 80 is connected to the current acquisition port of the processor unit 50. The current acquisition unit 40 is used for feeding the actual output current value of the smart power unit 20 back to I port of the processor unit 50.

The processor unit 50 controls the start or stop of the signal transmission and drive unit 60 by STA port, collects the actual power of the smart power unit 20 by V port and I port, gets a variety of commands by order port, and controls the actual output power of the smart power unit 20 by PWM port. The output power, the output voltage, the output current of the smart power can be controlled directly by PWM generated by external CPU, can also bring their own CPU, to achieve the adjustment of the output power, voltage and current by receiving external CPU command. In the detailed embodiments of the present invention, it is controlled directly by PWM generated by external CPU. In addition, the output, the output voltage and the output current can also be adjusted by frequency PFM.

The signal transmission and drive unit 60 is connected to the drive end of the power amplifier unit 80, to generate high-frequency drive signal to drive the power amplifier unit 80.

In the present application, the input control unit 70 is a keyboard input unit. The input control unit 70 can input a variety of commands including setting power, starting or stopping radio frequency output, work mode and etc., during the work process.

The work process of the present invention is divided into standby state and normal working state.

When in standby state, the state of each unit: after processor unit 50 received the command of stop output, the pulse width control port PWM of the processor unit 50 has been at a low level, the first transistor Q21 in the smart power unit 20 stays at cutoff state, then the output voltage $V_{20}$ of the smart power unit 20 will be zero. STA port of the processor unit 50 turns off the signal transmission and drive unit 60, two groups of high-frequency drive signals (DRV61, DRV64) and (DRV62, DRV63) of the signal transmission and drive unit 60 have no output, four groups of switching transistors (Q81, Q84) and (Q82, Q83) in the H-type full bridge drive unit are all at cutoff state. The collected data of current and voltage is zero. The output unit 90 has no energy input, and the load unit 100 has no energy injected.

When in normal working state, the state of each unit: (1) After the processor unit 50 received the command of start output, the pulse width control port PWM of the processor unit 50 will generate pulse width control signal with a frequency of $F=1/(T_{ON}+T_{OFF})$, and drive the switching transistor Q21 in the smart power unit 20 to work. The output voltage $V_{20}$ of the smart power unit 20 is no longer a value of zero. Wherein, $T_{ON}$ is conduction time of Q21, $T_{OFF}$ is cutoff time of Q21. (2) Meanwhile, STA port of the processor unit 50 will turn on the signal transmission and drive unit 60. (3) H-type full bridge drive unit is at working state under the drive of the signal transmission and drive unit 60. The detailed work process need not be repeated here. (4) The output unit 90 has high-frequency energy input, and it is conveyed to the load unit 100. (5) The voltage acquisition unit 30 feeds the actual output voltage value of the smart power unit 20 back to V port of the processor unit 50. The current acquisition unit 40 feeds the actual output current value of the smart power unit 20 back to I port of the processor unit 50. (6) The processor unit 50 calculates the actual output power of the smart power unit 20 according to $P_{20}=V*I$, calculates the real-time output data such as its impedance and etc., according to $R_{20}=V/I$. Since the energy loss of the power amplifier unit 80 and the output unit 90 is small, and the loss is predictable, after calculated $P_{20}$, the actual output power of the load can be obtained. Since the proportional relationship between the primary and secondary windings of the high frequency isolation transformer in the output unit 90 is known, after calculated $R_{20}$, the actual impedance value of the load can also be known. (7) The processor unit 50, according to the setting power provided by the keyboard input unit, compares with actual output power $P_{20}$, adjusts duty cycle D, to make the actual output power $P_{20}$ equal to the setting power. The detailed process is as follows. When the actual output power $P_{20}$ is greater than the setting power, reduce the duty cycle D, when the actual output power $P_{20}$ is less than the setting power, increase the duty cycle D, to make the output power $P_{20}$ be constantly at the value of setting power. Wherein, the duty cycle $D=T_{ON}/(T_{ON}+T_{OFF})$. (8) The processor unit 50, according to the value of real-time impedance $R_{20}$, determines whether the load unit 100 exceeds the expected impedance threshold or not, including the upper threshold and lower threshold, if one of the thresholds is exceeded, then make the duty cycle D be zero or minimum, stop radio frequency output or reduce output automatically, if within the normal range, without a stop command, continue the radio frequency output.

According to the experimental results, compare and analysis the high-frequency electric knife, the conventional radio frequency ablation device and the present application:

As shown in FIG. 5-1, FIG. 5-2 and FIG. 5-3, wherein APo refers to a curve that the output power changes with load in 100% power settings, BPo refers to a curve that the output power changes with load in 50% power settings, CPo refers to a curve that the output power changes with load in 10% power settings. The figures show that:

1. The devices of high-frequency electric knife class have no load range of constant output power, the output power fluctuates with the change of load, only suit for cutting and coagulating the target tissue. 2. The conventional radio frequency ablation device has load range of constant output power, but the range is narrow. Take FIG. 5-2 as an example, in the full power setting, the constant power load range is 25Ω-200Ω, which can meet the demand radio frequency ablation of liver tumors. If it is used for ablation treatment of target tissue other than liver, corresponding hardware circuits must be redesigned, to meet relevant constant power load range. For example, for cardiac ablation, the typical range is 70Ω-150Ω, for thyroid ablation, the typical range is 100Ω-500Ω, and for gastrointestinal tract ablation, the typical range is 150Ω-400Ω. 3. The constant power load range of the present invention is very wide. Take FIG. 5-3 as an example, even under full power setting, the constant power load range is within the range of 10Ω-800Ω, if under half power setting, the constant power load range is 10Ω-1500Ω. Given appropriate software modules, the present invention can be used for the radio frequency ablation treatment to the target tissue such as liver, heart, thyroid, gastrointestinal tract and etc., and also can be used for cutting and coagulation to the target tissue. The present invention can be widely used and has high versatility.

Figure 1:
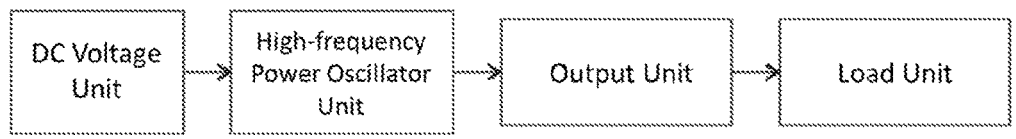
FIG. 1 is a schematic diagram of a high-frequency electric knife.
Figure 2:
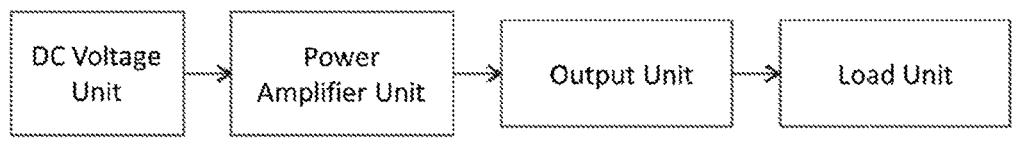
FIG. 2 is a schematic diagram of a conventional radio frequency ablation device.
Figures 1, 6:
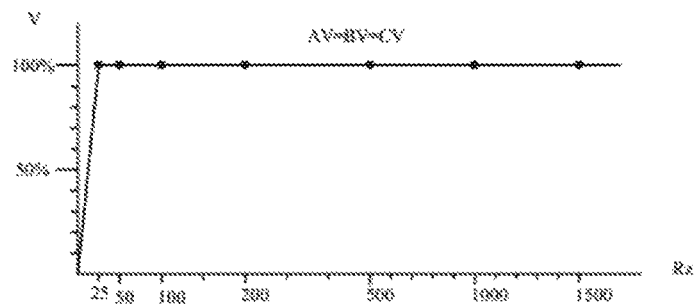
Figures 2, 6:
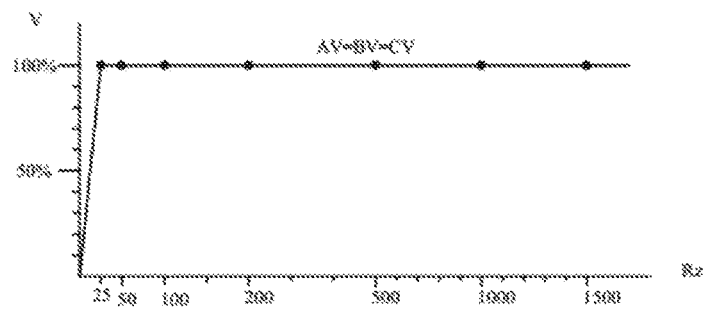
Figures 3, 6:
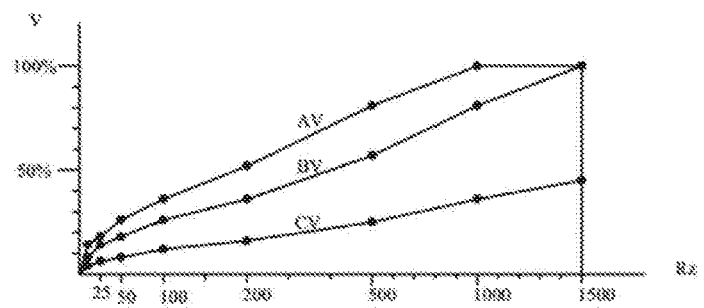
Figures 1, 7:
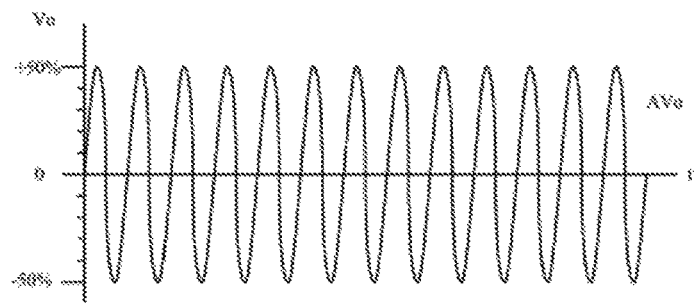
Figures 2, 7:
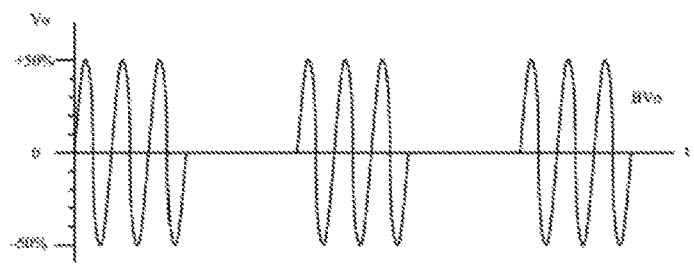
Figures 3, 7:
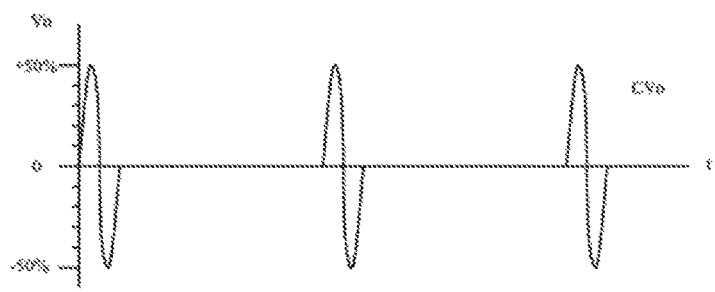
Figures 1, 8:
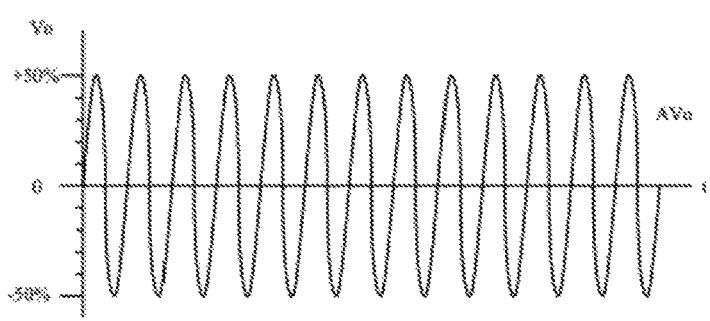
Figures 2, 8:
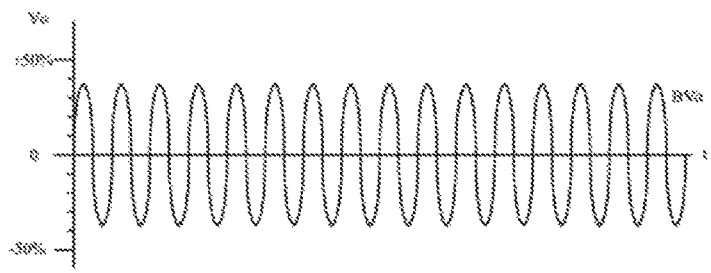
Figures 3, 8:
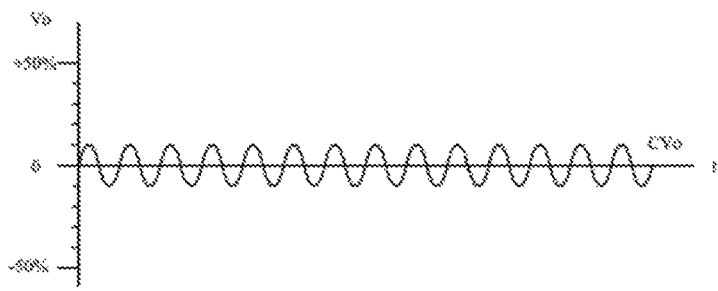
Figures 1, 9:
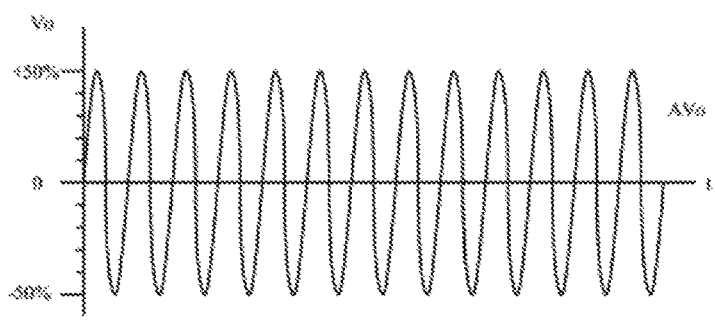
Figures 2, 9:
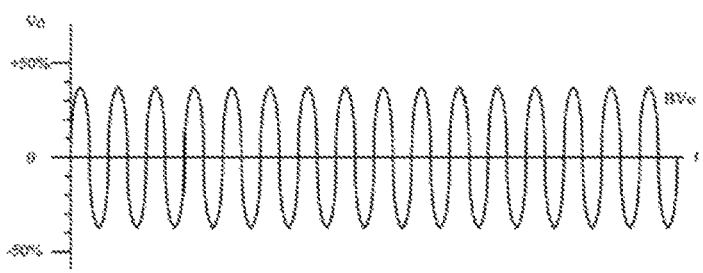
Figures 3, 9:
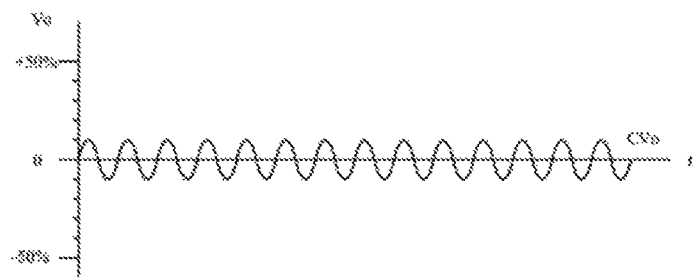

As shown in FIG. 6-1, FIG. 6-2 and FIG. 6-3, wherein AV refers to a curve that the DC input voltage value of high power oscillator unit or power amplifier unit 80 changes with load in 100% power settings, BV refers to a curve that the DC input voltage value of high power oscillator unit or power amplifier unit 80 changes with load in 50% power settings, CV refers to a curve that the DC input voltage value of high power oscillator unit or power amplifier unit 80 changes with load in 10% power settings. The figures show that:

FIG. 6-1 shows that the value of the DC input voltage V of the power amplifier unit of the high-frequency electric knife is constant, whether the setting power changes or the load changes, or both change at the same time, the DC input voltage V is constant. FIG. 6-2 shows that the value of the DC input voltage V of the power amplifier unit of the conventional radio frequency ablation device is also constant, whether the setting power changes or the load changes, or both change at the same time, the DC input voltage V is constant. FIG. 6-3 shows that the value of the DC input voltage V of the power amplifier unit 80 of the present invention can be automatically adjusted, when the setting power changes or the load changes, or both change at the same time, the DC input voltage V is automatically adjusted to the voltage value matched with the both. Thus it can be seen that, the present invention has an essential difference in operational principle with the high frequency electric knife and the conventional radio frequency ablation device.

As shown in FIG. 7-1, FIG. 7-2 and FIG. 7-3, AVo refers to the output voltage waveform of the high-frequency electric knife in 100% power setting, BVo refers to the output voltage waveform of the high-frequency electric knife in 50% power setting, CVo refers to the output voltage waveform of the high-frequency electric knife in 10% power setting. The figures show that:

Since the DC input voltage of the power oscillator is constant, the high-frequency electric knife uses the time width of oscillation interval of the power oscillator to adjust the output power, the wider the time width of the interval, the smaller the output power, the narrower the time width of the interval, the smaller the output power. Regardless of the changes of output power and load, the transient peak-peak voltage that the load is subjected to is relatively constant, and the peak-peak voltage value is very high. The output waveform is intermittent high frequency wave. There is an essential difference between the conventional radio frequency ablation device and the present invention.

As shown in FIG. 8-1, FIG. 8-2 and FIG. 8-3, wherein AVo refers to the output voltage waveform of the radio frequency ablation device in 100% power setting, BVo refers to the output voltage waveform of the radio frequency ablation device in 50% power setting, CVo refers to the output voltage waveform of the radio frequency ablation device in 10% power setting. The figures show that:

The output waveforms of the conventional radio frequency ablation device and the present invention are all continuous high frequency waves, but the procedures or methods of implementing the both are essentially different. Since the DC input voltage of the power amplifier unit is constant, the power-amplifier tube of the conventional radio frequency ablation device just like a variable resistor Ron connected to the load in series. When the output power and the load changes, adjust to the power value required by the load by adjust the size of on resistance of the power-amplifier tube. The energy which the power-amplifier tube is subjected to is $P_{ON}=I_{ON}^2*R_{ON}$, wherein $I_{ON}$ is the current value flow through the power amplifier tube. The energy is directly converted to thermal energy by the power amplifier tube to be consumed. Due to the larger loss and fast temperature rising of the power amplifier tube, necessary heat radiating measure is required, such as radiator, cooling fan and etc., the reliability of the whole machine is poor.

As shown in FIG. 9-1, FIG. 9-2 and FIG. 9-3, wherein AVo refers to the output voltage waveform of the present invention in 100% power setting, BVo refers to the output voltage waveform of the present invention in 50% power setting, CVo refers to the output voltage waveform of the present invention in 10% power setting. The figures show that:

Since the value of the DC input voltage $V_{20}$ of the power amplifier unit 80 of the present invention can be automatically adjusted, when the setting power changes or the load changes, or both change at the same time, the DC input voltage $V_{20}$ is automatically adjusted to the voltage value matched with the both. The power amplifier tube of the power amplifier unit 80 always works at switch status, when the power amplifier tube is on, $R_{ON}\approx 0$, the energy which the power-amplifier tube is subjected to is $P_{ON}=I_{ON}^2*R_{ON}\approx 0$. In the actual circuit, the loss of power amplifier tube mainly comes from the switching losses at the moments of on and off. The skilled in this art should be aware, and need not be repeated here.

Figures 1, 10:
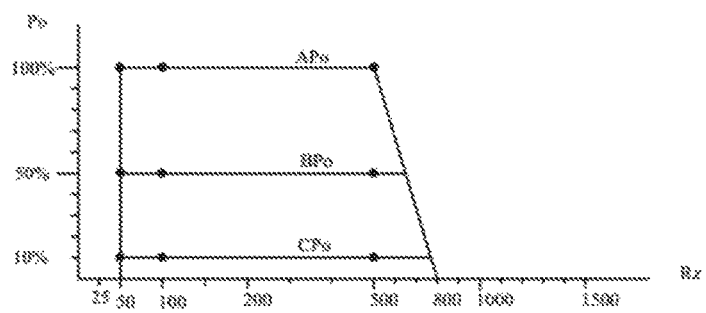
Figures 2, 10:
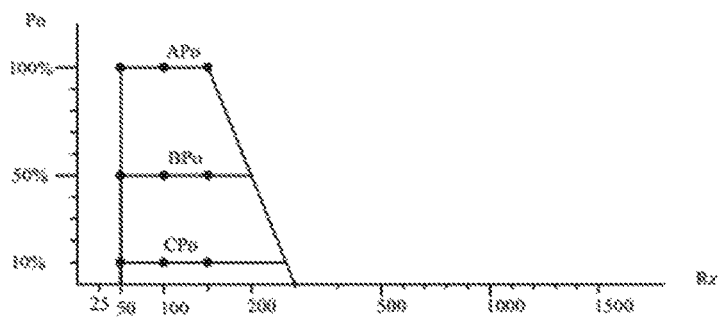
Figures 3, 10:
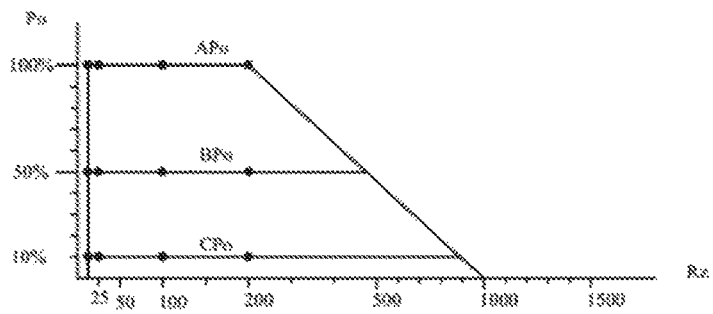
Figures 4, 10:
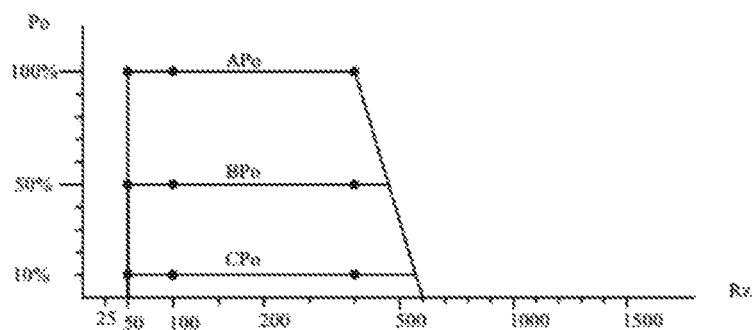
Figures 5, 10:
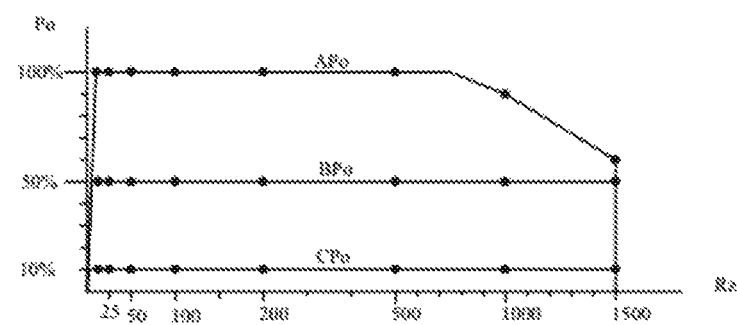

In summary, comparing the hardware circuits among the present invention, the high-frequency electric knife and the conventional radio frequency ablation device, there are essential differences among the topological structure, working principle and working process. The advantage of the present invention is obvious: (1) high reliability of the whole machine. In the embodiments of the present invention, all energy conversion units use the switching mode, and are all mature and simple topology, including H-type full bridge drive unit and intelligent power unit 20. Wherein all power amplifier tubes are at switch working status, the conversion efficiency is high, the losses of themselves are small, do not need special heat radiating measures such as fans, etc. The volume of whole machine can be reduced, and the waterproofing grade can be IP67 or more. (2) Output power control of hardware is simple, timely, and accurate. The actual output power can be output at a constant value as expected only by adjusting the duty cycle D of the smart power unit 20. (3) The data collection modes of the actual output voltage and current are simple, direct and reliable. Do not need special current and voltage collection coils, and also do not need nonlinear isolation components such as optical coupler, etc. (4) The range of the rated load of hardware is wide. In theory, the output power $P_{20}$ of the smart power unit 20 has nothing to do with the load, only relates to its duty cycle D, inductance $L_P$, pulse width frequency $F_{20}$ and input voltage $V_{10}$. That is $P_{20}=(D*V_{10})^2/(2*L_P*F_{20})$, the impedance values of various tissues of human body are all within the range of the rated load. (5) The versatility of hardware is strong, just by combining corresponding software modules, it can be used for the ablation, cutting, and coagulation to corresponding target tissue, referring to FIGS. 10-1 through 10-5, there are the curve graphs that the output power changes with load in different power settings when the present invention combined with corresponding software modules respectively used for thyroid ablation, cardiac ablation, liver ablation, gastrointestinal tract ablation, and cutting, coagulation to target tissue. Wherein APo refers to a curve that the output power changes with load in 100% power settings, BPo refers to a curve that the output power changes with load in 50% power settings, CPo refers to a curve that the output power changes with load in 10% power settings.

Furthermore, it can be used for various other uses and purposes of the present invention, within the scope of the present invention. It can be used in fields other than the present invention by slightly modifying the hardware circuit. For example, if the signal transmission and drive unit 60 is changed to ultrasonic frequency band, and the ultrasonic transducer is used as the load, the present invention becomes a power adjustable high-power ultrasonic generator or ultrasonic therapy device. If the signal transmission and drive unit 60 is changed to power frequency wave band, the present invention becomes an output power, or voltage, current adjustable high-performance inverter power supply. If the signal transmission and drive unit 60 is changed to audio frequency wave band, the present invention becomes an output power adjustable high power audio amplifier. Therefore, the use of the present invention in other fields is not limited.

A method of generating radio frequency energy using the radio frequency generator mentioned above, includes following steps:

S11: Providing DC power for the power amplifier by the smart power unit, and collecting the actual output voltage and the actual output current of the smart power unit, to obtain the actual output voltage and the actual output current of the smart power unit;

S12: Calculating the actual output power of the smart power unit based on $P_{20}=V*I$; calculating the actual impedance of the smart power unit based on $R_{20}=V/I$;

S13: According to the actual power obtained by the load unit $P_0=P_{20}-$(loss of power amplifier+loss of output unit), and the loss of the power amplifier and the loss of the output unit are known, and very small, the actual power obtained by the load unit can be calculated by the actual output power of the smart power unit.

S14: According to proportional relation between the primary and secondary windings of the high frequency isolation transformer in the output unit, the actual impedance of the load unit can be calculated by the actual impedance of the smart power unit.

S2: Comparing the actual output power of the smart power unit 20 with the preset power, when the actual output power of the smart power unit 20 is greater than the preset power, reduce the duty cycle; when the actual output power of the smart power unit 20 is less than the preset power, increase the duty cycle; keeping the actual output power of the smart power unit 20 and the preset power consistent.

Furthermore, the specific operations of step S3 is following:

S3: Comparing the actual impedance of the load unit with the threshold of the preset impedance, when the actual impedance of the load unit is greater than or equal to the lower threshold of the preset impedance and less than or equal to the upper threshold of the preset impedance, continue the radio frequency output; When the actual impedance of the load unit is less than the lower threshold of the preset impedance, the duty cycle of the smart power becomes zero, stop the radio frequency output; When the actual impedance of the load unit is greater than the upper threshold of the preset impedance, the duty cycle of the smart power becomes zero or minimum, stop the radio frequency output or reduce the radio frequency output.

What is claimed is:

1. A radio frequency generator, comprising:
   an input voltage unit, a smart power unit, a voltage acquisition unit, a power amplifier unit, an output unit and a load unit connected in sequence; a processor unit is connected between the voltage acquisition unit and the smart power unit; a current acquisition unit is set between the power amplifier unit and the processor unit; wherein:
   the input voltage unit is used for providing direct current (DC) voltage to the smart power unit;
   the smart power unit is used for providing variable DC voltage to the power amplifier unit;
   the voltage acquisition unit is used to collect the actual output voltage of the smart power unit;
   the current acquisition unit is used to collect the actual output current of the smart power unit;
   the processor unit is used to obtain the actual output power and actual impedance of the smart power unit, based on the collected actual output voltage and actual output current, and calculate the actual impedance and obtained actual power of the load unit, compare the actual output power of the smart power unit and the actual impedance of the load unit with a preset value respectively, and adjust the actual output voltage or actual output power of the smart power unit based on the result of comparison, to keep the actual output power of the smart power unit and the preset power consistent, to make the load unit get expected radio frequency energy; and
   a signal transmission and drive unit, is connected to a drive end of the power amplifier unit, to generate high-frequency drive signal to drive the power amplifier unit.

2. The radio frequency generator of claim 1, wherein the output voltage value, the output current value and the output power value of the smart power unit are not fixed, but can be adjusted freely.

3. The radio frequency generator of claim 2, wherein the smart power unit is a switching power converter, including a first capacitor, a first transistor, a second inductor, a third capacitor connected in parallel in order; a first inductor is connected in series between the positive end of the first capacitor and the drain of the first transistor, and the dotted terminal of the first inductor is connected to the positive terminal of the first capacitor; the grid of the first transistor is connected to the PWM-end of the processor unit; a second capacitor and a diode are connected in series in order between the opposite terminal of the second inductor and the third capacitor, and the cathode of the diode is connected to the positive end of the third capacitor, the positive end of the second capacitor is connected to the opposite terminal of the second inductor.

4. The radio frequency generator of claim 3, wherein the voltage acquisition unit comprises a first resistor and a second resistor, which are connected with each other in series and connected to both ends of the third capacitor in parallel, the connected node of the first resistance and the second resistance is connected to the voltage acquisition port of the processor unit.

5. The radio frequency generator of claim 3, wherein the current acquisition unit comprises a third resistor connected to the power amplifier unit, the connected node of the third resistor and the power amplifier unit is connected to the current acquisition port of the processor unit.

6. The radio frequency generator of claim 1, wherein the output unit includes a high frequency isolation transformer, a monitoring and controlling unit of auxiliary electrode and therapeutic electrode.

7. The radio frequency generator of claim 1, wherein the radio frequency generator further includes an input control unit connected to the processor unit for inputting control command.

8. A method of generating radio frequency energy using a radio frequency generator comprising:
an input voltage unit, a smart power unit, a voltage acquisition unit, a power amplifier unit, an output unit and a load unit connected in sequence; a processor unit is connected between the voltage acquisition unit and the smart power unit a current acquisition unit is set between the power amplifier unit and the processor unit wherein:
the input voltage unit is used for providing direct current (DC) voltage to the smart power unit;
the smart power unit is used for providing variable DC voltage to the power amplifier unit;
the voltage acquisition unit is used to collect the actual output voltage of the smart power unit;
the current acquisition unit is used to collect the actual output current of the smart power unit;
the processor unit is used to obtain the actual output power and actual impedance of the smart power unit, based on the collected actual output voltage and actual output current, and calculate the actual impedance and obtained actual power of the load unit, compare the actual output power of the smart power unit and the actual impedance of the load unit with a preset value respectively, and adjust the actual output voltage or actual output power of the smart power unit based on the result of comparison, to keep the actual output power of the smart power unit and the preset power consistent, to make the load unit get expected radio frequency energy; and
a signal transmission and drive unit, is connected to a drive end of the power amplifier unit, to generate high-frequency drive signal to drive the power amplifier unit;
wherein the method comprises the following steps:
S1: providing DC power for the power amplifier by the smart power unit, and collecting the actual output voltage and actual output current of the smart power unit, obtaining the actual output power and real time equivalent impedance of the smart power unit based on the collected information, and calculating the actual impedance and obtained actual power of the load unit;
S2: comparing the actual output power of the smart power unit with the preset power, adjusting the duty cycle of the smart power unit based on the result of comparison, to make the output power of the smart power unit be constant to the preset power; and
S3: comparing the actual impedance of the load unit with the threshold of preset impedance, then automatically controlling the radio frequency energy to continue to output or to stop to output based on the comparison result.

9. The method of generating radio frequency energy of claim 8, wherein the step S1 includes the following steps:
S11: providing DC power for the power amplifier by the smart power unit, and collecting the actual output voltage and the actual output current of the smart power unit, to obtain the actual output voltage and the actual output current of the smart power unit;
S12: calculating the actual output power of the smart power unit based on $P_{20}=V*I$; calculating the actual impedance of the smart power unit based on $R_{20}=V/I$;
S13: according to the actual power obtained by the load unit $P_0=P_{20}-$(loss of power amplifier+loss of output unit), and the loss of the power amplifier and the loss of the output unit are known, and very small, the actual power obtained by the load unit is calculated by the actual output power of the smart power unit; and
S14: according to proportional relation between the primary and secondary windings of a high frequency isolation transformer in the output unit, the actual impedance of the load unit is calculated by the actual impedance of the smart power unit.

10. The method of generating radio frequency energy of claim 8, wherein the operations of step S2 comprise:
S2: comparing the actual output power of the smart power unit with the preset power, when the actual output power of the smart power unit is greater than the preset power, reduce a duty cycle of the smart power unit; when the actual output power of the smart power unit is less than the preset power, increase the duty cycle of the smart power unit; keeping the actual output power of the smart power unit and the preset power consistent.

11. The method of generating radio frequency energy of claim 8, wherein the operations of step S3 comprise:
comparing the actual impedance of the load unit with the threshold of the preset impedance, when the actual impedance of the load unit is greater than or equal to the lower threshold of the preset impedance and less than or equal to the upper threshold of the preset impedance, continue output of the radio frequency energy; when the actual impedance of the load unit is less than the lower threshold of the preset impedance, the duty cycle of the smart power unit becomes zero, stop the output of the radio frequency energy; when the actual impedance of the load unit is greater than the upper threshold of the preset impedance, the duty cycle of the smart power becomes zero or minimum, stop or reduce the output of the radio frequency energy.

* * * * *